United States Patent [19]

Ohkawa et al.

[11] Patent Number: 4,826,281
[45] Date of Patent: May 2, 1989

[54] OPTICAL CABLE WITH BENDING MECHANISM

[75] Inventors: Shinichi Ohkawa; Kunio Awazu, both of Osaka, Japan

[73] Assignee: Sumitomo Electric Industries, Ltd., Osaka, Japan

[21] Appl. No.: 93,658

[22] Filed: Sep. 8, 1987

[51] Int. Cl.⁴ .............................................. G02B 23/26
[52] U.S. Cl. ................................ 350/96.26; 350/96.25
[58] Field of Search ............... 350/96.26, 96.29, 96.30, 350/96.23, 96.25; 128/4, 6, 635; 356/241

[56] References Cited

U.S. PATENT DOCUMENTS

| | | | |
|---|---|---|---|
| 4,530,078 | 7/1985 | Lagakos et al. | 350/96.29 |
| 4,575,185 | 3/1986 | Wentzell et al. | 350/96.26 |
| 4,708,434 | 11/1987 | Tsuno | 350/96.26 |
| 4,735,501 | 4/1988 | Ginsburgh et al. | 350/96.26 |

Primary Examiner—William L. Sikes
Assistant Examiner—B. Randolph Holloway
Attorney, Agent, or Firm—Cushman, Darby & Cushman

[57] ABSTRACT

An optical cable of the present invention comprises: an optical fiber sensor, the optical fiber sensor having an optical fiber having an external circumferential wall portion and a flexible coating film covering the external circumferential wall portion; and a tube member with a good flexibility, the tube member having an axis and an internal circumferential wall portion and receiving the optical fiber sensor along the axis such that the coating film faces the internal circumferential wall portion of the tube member, the tube member having a portion where the axis is bent; wherein fluid is sealed in between the coating film and the internal circumferential wall portion of the tube member with its pressure being changeable.

6 Claims, 2 Drawing Sheets

OPTICAL CABLE WITH BENDING MECHANISM

BACKGROUND OF THE INVENTION

This invention relates to a cable with a bending mechanism, and more particularly to a cable useful as an optical fiber sensor such as is used in a medical or industrial endoscope or to a laser beam surgical catheter.

In an optical fiber sensor such as is used in a medical or industrial endoscope, it is often required to externally operate the fiber sensor such that the fiber sensor is bent at its end portion to let an image pickup portion provided at the end portion face in a desired direction so as to pick up a desired image.

To meet this demand, an optical fiber sensor shown in FIG. 1 has been developed. As shown in FIG. 1, a plurality of knucle rings 6 are provided to encircle the fiber sensor body 8. The knucle rings 6 come into contact with one another at protruded support portions 7 provided in the center portions of the rings 6. Several operating wires 5 are provided at the peripheral portions of the knucle rings 6 in a symmetrical manner. According to such a structure of the optical fiber sensor, by tightening or pulling up one or many of the wires 5 but extending other one or many of the wires, the end portion of the fiber is bent to let the image pickup portion at the end portion thereof face in a desired direction.

However, the conventional optical fiber sensor having the above-described structure has such a problem that the fiber sensor as a whole is made thick by the use of the knucle rings 6. To the contrary, recently it has become possible to produce a very long but very thin image fiber which is used as a body of the optical fiber sensor.

SUMMARY OF THE INVENTION

An object of the present invention is to solve the above-described problems of the conventional optical fiber sensor. That is, the object of the present invention is to provide an optical fiber sensor with a bending mechanism which has a small diameter and a relatively simple structure and is operable to bend at its tip end.

In order to achieve the above-mentioned object and other objects, the optical cable of the present invention comprisies: an optical fiber sensor body, the optical fiber sensor body having an optical body with an external circumferential wall portion and a flexible coating film covering the external circumferential wall portion; and a tube member with a good flexibility, the tube member having an axis and an internal circumferential wall portion and receiving the optical fiber sensor along the axis such that the coating film faces the internal circumferential wall portion of the tube member, the tube member having a portion where the axis is bent; wherein the fluid is sealed in a fluid passage between the coating film and the internal circumferential wall portion of the tube member, the pressure inside the fluid passage is changeable. The tube member is bent at the end of the portion thereof.

DETAILED DESCRIPTION OF THE PREFERRED EMBODIMENT

An optical cable with a bending mechanism of an embodiment of the present invention will be described in detail hereunder, with reference to the accompanying drawings.

Figure 1:
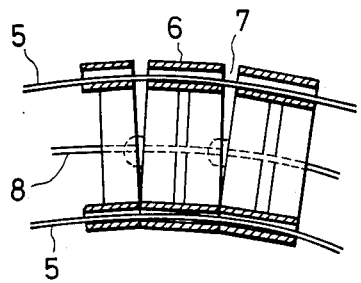
FIG. 1 is an explanatory view of a conventional optical fiber sensor.
Figure 2:
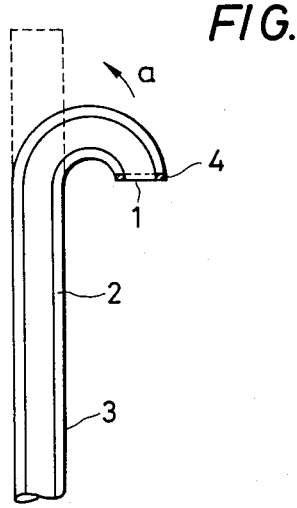
FIG. 2 is a vertical sectional view of an optical fiber sensor cable of an embodiment of the present invention.
Figure 3:
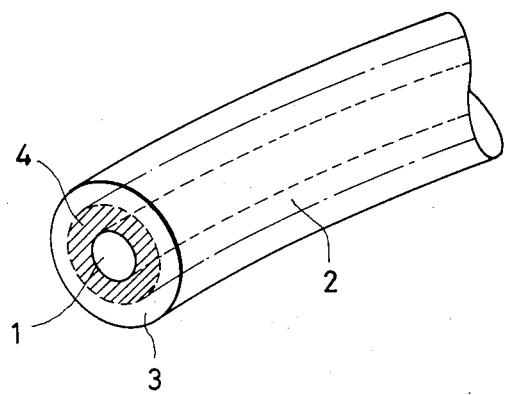
FIG. 3 is a view showing externally the fiber sensor cable of FIG. 2.

FIG. 2 is a vertically sectional view outlining the optical cable with a bending mechanism of an embodiment of the present invention. FIG. 3 is a perspective view showing a tip end portion of the optical cable of FIG. 2. In FIG. 2, the optical fiber sensor body 1 is inserted into a tube 3 having excellent bending characteristic or flexibility made of plastic such as polyethylene, rubber such as silicone rubber, or the like.

The optical fiber sensor 1 is previously bent at its end portion with a desired radius of curvature, so that the tube 3 is in a shape indicated by a solid line in FIG. 2. When a fluid passage 2 is filled with liquid or gas, since the space 2 is closed at its tip end with a stopper or plug 4, the internal pressure of the fluid passage 2 is increased to thereby bend the tube 3 and stopper 4 in a direction a in FIG. 2.

According to the optical fiber sensor of the present invention, by the above-described structure, the degree of bending of the fiber sensor 1 changes with changes in the internal pressure of the fluid passage 2.

The above description is made to an embodiment of the present invention applied to an optical fiber sensor having an image sensor as its body. The above-described bending mechanism is further applicable to an optical cable in which an energy fiber made of AgBr, AgCl which transmit $CO_2$ laser beam therethrough, or the like is inserted with or without the image fiber. If the bending mechanism of the present invention is applied to the end portion of the cable having such an energy transmitting fiber therein, it becomes possible to freely change the laser beam irradiation direction so that it makes it possible to apply the laser beam to any affected part on a body as a laser beam medical treatment.

Figure 4:
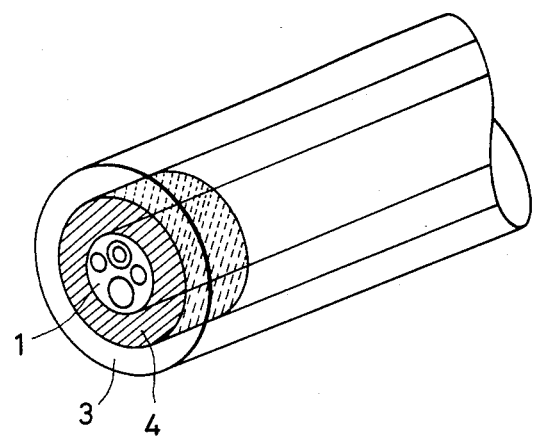
FIG. 4 is a view illustrating an end portion of the optical fiber cable of FIG. 2.
Figure 5:
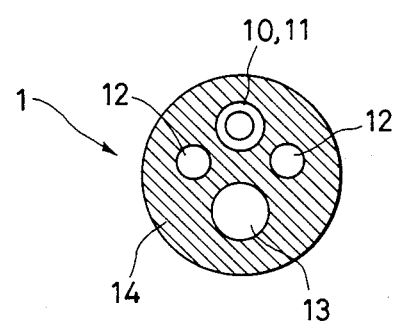
FIG. 5 is a front view of the end portion of the optical fiber cable of FIG. 4.

FIG. 4 shows one example of the optical fiber cable of the embodiment of the present invention used as a medical endoscope. FIG. 5 shows the end portion of the optical fiber cable of FIG. 4. In FIG. 4, a tube made of polyurethane resin having stainless braided wires therein is used for the tube 3. The optical fiber sensor 1 comprises a group of elemental fibers coated with polyurethane resin 14. The group of elemental fibers includes an image transmitting bundle fiber 10, an objective lens group 11 provided at the end portion of the image transmitting bundle fiber 10, an illumination light transmitting fiber 12 and a laser beam transmission fiber 13, as shown in FIG. 5.

As shown in FIG. 4, the stopper 4 made of polyurethan resin is provided at the end of the optical fiber cable. The illumination light transmission fiber 12 is made of silicone resin. The image transmission bundle fiber 10 comprises a bundle of three thousand elemental fibers of multi-compound glass, at the end portion of which a lens 11 made of optical glass is provided and held at an optical position with a holding sleeve. In a laser beam transmission fiber 13, an optical fiber of pure quartz series having a core diameter of 200 micron is used.

As described above, according to the bending mechanism of the optical cable of the present invention, it becomes possible to freely let the tip end of the fiber sensor face in a desired direction. The optical cable of the present invention is made simple in construction and has a small diameter.

Various modifications and variations could be made in the invention without departing from the scope or spirit thereof.

We claim:

1. An optical cable, comprising:
   an optical fiber sensor body having an optical fiber sensor with a flexible external circumferential wall portion; and
   a flexible tube member having an axis and an internal circumferential wall portion disposed to receive said optical fiber sensor body along said axis such that said external circumferential wall portion faces said internal circumferential wall portion of said tube member, said tube member having a bent portion at one end thereof and a fluid passage extending along the axis thereof;
   wherein when fluid is provided in said fluid passage said bent portion is straightened by a change in pressure produced by said fluid inside said fluid passage.

2. An optical cable of claim 1, wherein said optical fiber sensor body has an end portion, said tube member has an end portion facing said end portion of said optical fiber sensor body, and said portion where said axis of said tube member is bent is said end portion of said tube member.

3. An optical cable of claim 2, further comprising a stopper member provided at an end portion of said fluid passage, said stopper member preventing the fluid from flowing out said end portion of said fluid passage.

4. An optical fiber sensor of claim 1, wherein said fiber sensor has an image transmission fiber and an irradiation beam transmission fiber.

5. An optical fiber sensor of claim 1, wherein said fiber sensor is selected from an image fiber and an energy fiber.

6. An optical fiber sensor of claim 4, wherein said fiber sensor is selected from an image fiber and an energy fiber.

* * * * *